United States Patent [19] [11] 4,028,349
Partridge, Jr. et al. [45] June 7, 1977

[54] SYNTHESES OF 24R,25- AND 24S,25-DIHYDROXYCHOLESTEROL 24,25-KETALS AND ALKANOYL DERIVATIVES THEREOF

[75] Inventors: John Joseph Partridge, Jr.; Milan Radoje Uskokovic, both of Upper Montclair, N.J.

[73] Assignee: Hoffmann-La Roche Inc., Nutley, N.J.

[22] Filed: Mar. 8, 1976

[21] Appl. No.: 664,833

[52] U.S. Cl. .................. 260/239.55 D; 260/397.2; 260/239.55 R
[51] Int. Cl.[2] ........................................ C07J 71/00
[58] Field of Search ............... 260/239.55 D, 397.2

[56] References Cited

UNITED STATES PATENTS 3,644,341 2/1972 Fried .................. 260/239.55 D
3,766,256 10/1973 Uskokovic ............. 260/239.55 D

*Primary Examiner*—Elbert L. Roberts
*Attorney, Agent, or Firm*—Samuel L. Welt; George M. Gould; Raymond R. Wittekind

[57] ABSTRACT

Syntheses of 24R,25- and 24S,25-dihydroxycholesterol 24,25-ketals and alkanoyl derivatives thereof, intermediates in the preparation of the biologically important metabolite and derivative, respectively, of vitamin $D_3$, are described.

33 Claims, No Drawings

SYNTHESES OF 24R,25- AND 24S,25-DIHYDROXYCHOLESTEROL 24,25-KETALS AND ALKANOYL DERIVATIVES THEREOF

BACKGROUND OF THE INVENTION

The isolation and characterization of 24,25-dihydroxycholecalciferol (24,25-dihydroxyvitamin $D_3$) (M. F. Holick et al., Biochemistry, 11, 4251 [1972]), and the subsequent finding that this second most abundant metabolite of vitamin $D_3$ (J. L. Omdahl and H. F. DeLuca, Physiological Reviews, 53, 327 [1973]) preferentially stimulates intestinal calcium transport without, at comparable dose levels, mobilizing bone calcium, prompted extensive investigation of the physiological role played by this metabolite (see, for example, H. K. Schnoes and H. F. DeLuca, Vitamins and Hormones, 32, 395 [1974]). These investigations have been hampered by the minute amounts of the metabolite available from natural sources, the lack of information concerning the stereochemistry of the metabolic hydroxyl group at C-24 and the effect of the configuration of this group on the biological activity exhibited by 24,25-dihydroxycholecalciferol.

In 1973, M. Seki et al., Chem. Pharm. Bull. (Japan), 21, 2783(1973) described the conversion of desmosterol acetate to $24\xi,25$-dihydroxycholesterol, a precursor of 24,25-dihydroxycholecalciferol. Shortly thereafter, H. -Y. Lam et al., Biochemistry, 12, 4851 (1973) and J. Redel et al., Compt. rend. Acad. Soc. (Paris), 278, 529 (1974) disclosed syntheses of $24\xi,25$-dihydroxycholecalciferol starting from $3\beta$-acetoxy-27-nor-5-cholesten-25-one and desmosterol acetate, respectively. These syntheses are non-stereospecific yielding mixtures of stereoisomers at C-24. M. Seki et al., Tetrahedron Letters, 15 (1975) recently described the separation of $24\xi,25$-dihydroxycholesterol into the 24R- and 24S-isomers and the conversion of the 24R- and 24S-isomer into 24R,25- and 24S,25-dihydroxycholecalciferol, respectively. This synthesis suffers from the inherent disadvantages associated with the separation step. Thus, stereospecific syntheses of 24R,25- and 24S,25-dihydroxycholecalciferol utilizing 24,25-dihydroxycholesterol derivatives of known stereochemistry at C-24 overcoming the deficiencies of the prior art processes and making this important metabolite of vitamin $D_3$ readily available for biological, clinical and therapeutic use would represent an important contribution to the advancement of the state of the art in the vitamin D field.

DETAILED DESCRIPTION OF THE INVENTION

The present invention relates to novel, efficient processes for the preparation of 24R,25- and 24S,25-dihydroxycholesterol 24,25-ketals and alkanoyl derivatives thereof starting from precursors readily available from natural sources. More particularly, the present invention relates to processes for the preparation of 24R,25- and 24S,25-dihydroxycholesterol 24,25-ketals and alkanoyl derivatives thereof comprising, as the key steps of each process, ketalization of 24R,25- and 24S,25-dihydroxy-$6\beta$-hydroxy- or substituted $6\beta$-hydroxy-$3\beta$,5-cyclo-$5\alpha$-cholestane, ketalization of 24R,25- and 24S,25-dihydroxycholesterol or stereospecific cleavage of 24R,25- and 24S,25-epoxy-$6\beta$-hydroxy- or substituted $6\beta$-hydroxy-$3\alpha$,5-cyclo-$5\alpha$-cholestane wih concomitant retro-i-steroid rearrangement.

As used throughout the specification and the appended claims, the term "alkyl group" refers to a monovalent substituent consisting solely of carbon and hydrogen of from 1 to 20 carbon atoms which may be straight or branched-chain. Examples of alkyl groups are methyl, ethyl, n-propyl, i-propyl, tert.-butyl, hexyl, octyl and so forth. The term "alkylene group" refers to a divalent substituent consisting solely of carbon and hydrogen of from 1 to 20 carbon atoms which may be straight or branched-chain and whose free valences are attached to two distinct groups. Examples of alkylene groups are methylene, ethylene, propylene and so forth. The term "alkoxy group" refers to a monovalent substituent which consists of an alkyl group linked through an ether oxygen having its free valence bond from the ether oxygen. Examples of alkoxy groups are methoxy, ethoxy, isopropoxy, tert.-butoxy and so forth. The term "phenyl alkoxy" refers to an alkoxy group which is substituted by a phenyl ring. Examples of phenyl alkoxy groups are benzyloxy, 2-phenylethoxy, 4-phenylbutoxy and so forth. The term "alkanoyloxy group" refers to the residue of an alkylcarboxylic (alkanoic) acid formed by removal of the hydrogen from the hydroxyl portion of the carboxyl group. Examples of alkanoyloxy groups are formyloxy, acetoxy, butyryloxy, hexanoyloxy and so forth. The term "alkanol" refers to a compound formed by combination of an alkoxy group and a hydrogen atom. Examples of alkanols are methanol, ethanol, 2-propanol and so forth. The term "alkanone" refers to a compound formed by removal of the hydroxylic proton and that adjacent to the hydroxyl group. Examples of alkanones are acetone, 2-propanone, 3-pentanone and so forth. The term "lower" as applied to any of the aforementioned groups, refers to those groups having from 1 to 8 carbon atoms.

In the formulas presented herein, the various substituents are illustrated as joined to the steroid nucleus by one of these notations: a solid line (—) indicating a substituent which is in the $\beta$-orientation (i.e., above the plane of the molecule), a dotted line (-----) indicating a substituent which is in the $\alpha$-orientation (i.e., below the plane of the molecule), or a wavy line ( $\sim$ ) indicating a substituent which may be in the $\alpha$ - or $\beta$-orientation. The formulas have all been drawn to show the compounds in their absolute stereochemical configurations. Since the starting materials are derived from naturally occurring stigmasterol, the products exist in the single absolute configuration depicted herein. However, the processes of the present invention are intended to apply as well to the synthesis of steroids of the "unnatural" and racemic series, i.e., the enantiomers of the compounds depicted herein and mixtures of both. Thus, one may begin the synthesis utilizing "unnatural" or racemic starting materials to prepare "unnatural" or racemic products, respectively. Optically active products can then be prepared by resolution of the racemic products utilizing in the preparation thereof standard resolution techniques well known in the steroid art.

The Greek letter xi ($\xi$) in the name of a vitamin $D_3$ intermediate or metabolite indicates that the stereochemistry of the substituent to which it refers is undefined or that the product consists of a mixture of compounds epimeric at the designated position.

The nomenclature adopted to define absolute configuration of substituents bound to carbon atom 24 of the steroid nucleus is described in the Journal of Organic Chemistry, 35, 2849 (1970) under the title "IUPAC Tentative Rules for the Nomenclature of Organic Chemistry. Section E. Fundamental Stereochemistry".

The starting material, a compound of the formula

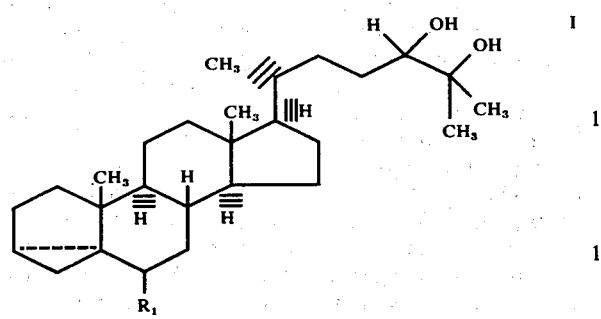

wherein $R_1$ is hydroxy, lower alkoxy, phenyl lower alkoxy, lower alkanoyloxy or benzoyloxy, and the absolute configuration at C-24 is R or S for the first process for the preparation of 24R,25- and 24S,25-dihydroxycholesterol 24,25-ketals and alkanoyl derivatives thereof is synthesized by the method described in U.S. pat. application Ser. No. 621,319 filed Oct. 10, 1975.

In the first step of this sequence, the 24,25-diol function of the compound of formula I is ketalized to the compound of the formula

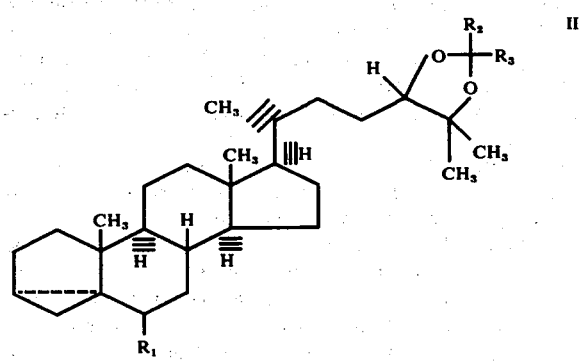

wherein $R_1$ is as above, $R_2$ and $R_3$ each independently are lower alkyl, $R_2$ and $R_3$ taken together are lower alkylene and the absolute configuration at C-24 is R or S without concomitant retro-i-rearrangement.

This transformation is conveniently performed by treating a compound of formula I with a compound of the formula

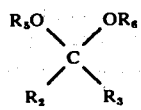

wherein $R_2$ and $R_3$ are as above, $R_5$ and $R_6$ each taken independently are lower alkyl and $R_5$ and $R_6$ taken together are lower alkylene in the presence of an acid catalyst and inert solvent.

As suitable acid catalysts there may be mentioned mineral acids such as hydrochloric acid, hydrobromic acid, sulfuric acid and the like; and organic sulfonic acids such as methanesulfonic acid, benzenesulfonic acid, paratoluenesulfonic acid and the like. Organic sulfonic acids are preferred. Para-toluenesulfonic acid is most preferred.

As suitable inert organic solvents there may be mentioned alkanols such as methanol, ethanol, 2-propanol and the like; and alkanones of the formula

wherein $R_2$ and $R_3$ are as above such as acetone, 2-butanone, 3-pentanone, cyclohexanone and the like. It is preferred to employ the alkanone of formula IV corresponding to the ketal of formula III as the inert solvent in the exchange ketalization reaction. For example, when 3-pentanone ketal is employed as the ketalizing agent, it is preferred to employ 3-pentanone as the solvent. The combination of 2,2-dimethoxypropane and acetone is most preferred.

While the exchange ketalization reaction temperature is not narrowly critical, it is desirable to carry out the reaction at reduced temperature to avoid retro-i-steroid rearrangement of the 6 β-hydroxy- or substituted 6 β-hydroxy-3α,5-cyclo-5α-system of the starting material. A reduced temperature of between about −20° and +20° C. is preferred. A reduced temperature of about 0° C. is most preferred.

In the second and last step of this process, the i-steroid of formula II is rearranged to the compound of the formula

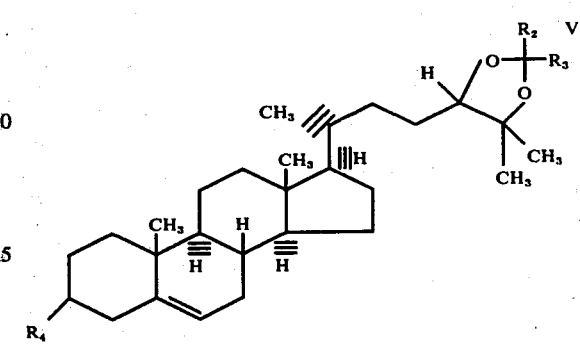

wherein $R_2$ and $R_3$ are as above, $R_4$ is lower alkanoyloxy and the absolute configuration at C-24 is R or S by methods well known in the art involving the solvolysis of the i-steroid moiety in the presence of an alkanoic acid and its corresponding alkali metal salt at an elevated temperature. For example, to prepare a compound of formula V wherein $R_4$ is acetoxy, one employs acetic acid and sodium or potassium acetate at a reaction temperature from about 40° to about 100° C. A reaction temperature of from about 40° to about 80° C. is preferred, a reaction temperature of about 60° C. being particularly preferred.

Alternatively, a compound of formula V can be prepared by concomitant cleavage of the epoxy moiety and rearrangement of the i-steroid function of a compound of the formula

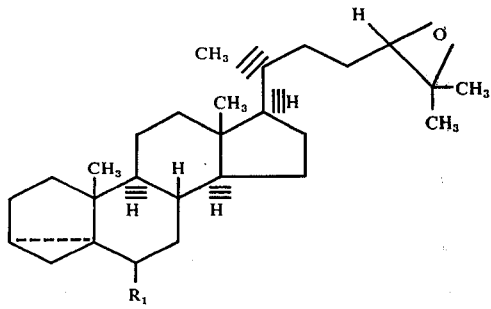

wherein $R_1$ is as above and the absolute configuration at C-24 is R or S
to a compound of the formula

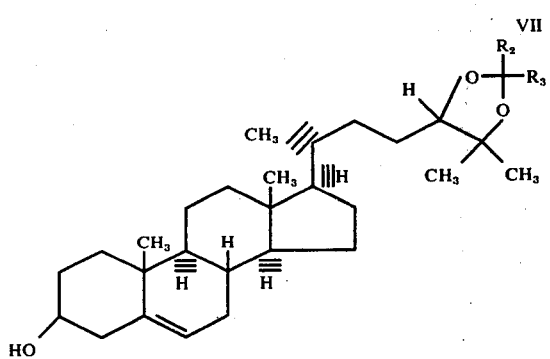

wherein $R_2$ and $R_3$ are as above
followed by acylation of a compound of formula VII by methods well known in the art. See, for example, R. B. Wagner and H. D. Zook, "Synthetic Organic Chemistry", John Wiley and Sons, Inc., New York, N.Y. 1953, pages 480 to 483.

The cleavage-rearrangement reaction is conveniently conducted by treating a compound of formula VI with a compound of the formula

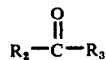

IV wherein $R_2$ and $R_3$ are as above
in the presence of a strong acid followed by quenching under basic conditions.

Suitable strong acids include mineral acids such as hydrogen chloride, hydrogen bromide and the like; and Lewis acids such as aluminum chloride, ferric chloride, zinc chloride, stannic chloride and the like. Lewis acids are preferred. Stannic chloride is most preferred.

The reaction temperature is not narrowly critical. However, it is preferred to conduct the cleavage-rearrangement at a reduced temperature to avoid undesirable side reactions. A reaction temperature within the range of about −20° to +20° C. is preferred, a reaction temperature of about 0° C. being most preferred.

The cleavage-rearrangement reaction is preferably performed in the presence of excess reactant of formula IV, the compound of formula IV acting as both the reactant and the reaction medium. For example, to prepare a compound of formula VII wherein $R_2$ and $R_3$ are methyl, one employs acetone as the ketalizing agent and as the reaction solvent. Similarly, if one desires to prepare a compound of formula VII wherein $R_2$ is methyl and $R_3$ is ethyl, one employs 2-butanone as the ketalizing agent and reaction medium.

The hydrolysis of the cleavage-rearrangement reaction product is conducted by treating the reaction mixture with aqueous alkali at reduced temperatures to control the decomposition of the reaction intermediate and thereby prevent formation of undesirable by-products. Suitable bases include alkali and alkaline earth hydroxides, alkoxides such as methoxides, ethoxides and the like, and salts of weak organic acids as carbonates, acetates and the like. Salts of weak organic acids are preferred. Sodium acetate is most preferred. The hydrolysis is preferably performed within the temperature range of −20° to +20° C., most preferably at about 0° C.

The epoxides of formula VI, the starting materials for the synthesis of 24R,25- and 24S,25-dihydroxycholesterol 24,25-ketals and alkanoyl derivatives thereof by the second process, are readily prepared by methods described in U.S. patent application Ser. No. 621,319, filed Oct. 10, 1975.

In still another process for the preparation of 24R,25- and 24S,25-dihydroxycholesterol 24,25-ketals and alkanoyl derivatives thereof, 24,25-dihydroxycholesterol of the formula

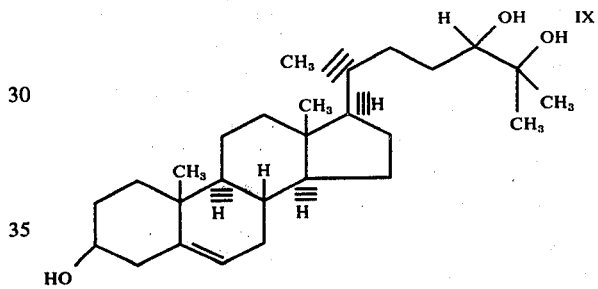

wherein the absolute configuration at C-24 is R or S is ketalized with a compound of formula III to afford a compound of formula VII followed by acylation of the free hydroxyl group by methods known per se for such reactions (see R. B. Wagner and Zook, supra) to afford the compound of formula V.

The ketalization is conveniently conducted in the presence of an acid catalyst and an inert solvent. Suitable acid catalysts include mineral acids such as hydrochloric acid, hydrobromic acid, sulfuric acid; an organic sulfonic acids such as methanesulfonic acid, benzenesulfonic acid and the like. Organic sulfonic acids are preferred. Para-toluenesulfonic acid is most preferred. Suitable inert solvents include alkanols such as methanol, ethanol, 2-propanol and the like; and alkanones having the same carbon skeleton as the ketalizing agent. For example, acetone is employed as the reaction medium when acetone ketal is employed as the ketalization agent. The reaction may also be performed in excess ketalizing agent.

The ketalization reaction temperature is not critical. However, it is desirable to conduct the reaction at a reduced temperature to prevent undesirable side reactions such as dehydration. A reduced temperature of about −20° to +25° C. is preferred. Most preferred is a temperature of about 0° C.

The synthesis of 24R,25-and 24S,25-dihydroxycholesterol, the starting material for the preparation of 24R,25-and 24S,25-dihydroxycholesterol 24,25-ketals and alkanoyl derivatives thereof by the third process is described in U.S. patent application Ser. No. 621,319 filed Oct. 10, 1975.

24R,25- and 24S,25-dihydroxycholesterol 24,25-ketals and the alkanoyl derivatives thereof are useful intermediates for the elaboration of the biologically important metabolite of vitamin $D_3$, 24R,25-dihydroxycholecalciferol and the unnatural 24S stereoisomer. The transformation of the cholesterol 24,25-ketals to the 24,25-dihydroxycholecalciferols is accomplished by introduction of the $\Delta^7$-double bond, generally by a halogenation-dehydrohalogenation process, followed by photolysis of the diene, thermal rearrangement of the previtamin and cleavage of the ketal and hydrolysis of the ester function. These conversions are described in U.S. patent applications identified as Ser. Nos. 664,799 and 664,848, filed on Mar. 8, 1976.

The following examples are illustrative of the invention and are not to be construed as limiting the invention in any manner.

EXAMPLE 1

24R,25-Dihydroxy-6β-methoxy-3α,5-cyclo-5α-cholestane 24,25-acetonide

A mixture of 0.430 g. (0.0010 mole) of 24R,25-dihydroxy-6β-methoxy-3α,5-cyclo-5α-cholestane, 1.0 ml (0.010 mole) of 2,2-dimethoxypropane, 9 ml. of acetone and 0.010 g. of p-toluenesulfonic acid monohydrate was stirred at 0° C. for 2 hours. The mixture was diluted with 25 ml. of methylene chloride and this solution was washed with 10 ml. of saturated aqueous sodium bicarbonate solution and 10 ml. of water. The solution was then dried over anhydrous magnesium sulfate, filtered and evaporated to dryness. The residue was recrystallized from methanol to yield 0.380 g. (81%) of 24R,25-dihydroxy-6β-methoxy-3α,5-cyclo-5α-cholestane 24,25-acetonide, m.p. 108°–109°; $[\alpha]_D^{25}$ +44.5° (c 1.00, CHCl$_3$).

EXAMPLE 2

24R,25-Dihydroxycholesterol 24,25-acetonide

A mixture of 0.100 g. (0.00025 mole) of 24R,2525-epoxy-6β-methoxy-3α,5-cyclo-5α-cholestane, 4 ml. of acetone and 0.005 g. of stannic chloride was stirred at 0°C. for 2 hours, A total of 1 ml. of saturated aqueous sodium acetate solution was added and the mixture was stirred at 0° C. for 5 minutes. The mixture was diluted with 10 ml. of water. The solution was extracted with 3 × 10 ml. of methylene chloride. The combined organic layers were washed with 2 × 10 ml. of saturated aqueous sodium bicarbonate solution. The organic layers were then dried over anhydrous magnesium sulfate, filtered and concentrated under vacuum. The residue was recrystallized from acetone to give 0.094 g. (82%) of 24R,25-dihydroxycholesterol 24,25-acetonide, m.p. 153°–154°; $[\alpha]_D^{25}$ −42.9° (c 1.00, CHCl$_3$).

EXAMPLE 3

24R,25-Dihydroxycholesterol 24,25-acetonide

A mixture of 0.084 g. (0.00020 mole) of 24R,25-dihydroxycholesterol, 4 ml. of 2,2-dimethoxypropane and 0.010 g. of p-toluenesulfonic acid monohydrate was stirred at 0° for 1 hour. A total of 4 ml. of methanol was added and the mixture was stirred at 25° for 1 hour. The mixture was diluted with 10 ml. of saturated aqueous sodium bicarbonate solution and extracted with 2 × 25 ml. of methylene chloride. The organic layers were washed with 25 ml. of water and dried over anhydrous magnesium sulfate. Evaporation of solvent and recrystallization of the residue from acetone afforded 0.084 g. (92%) of 24R,25-dihydroxycholesterol 24,25-acetonide, m.p. 153°–154°; $[\alpha]_D^{25}$ −42.5° (c 0.98, CHCl$_3$).

EXAMPLE 4

24S,25-Dihydroxy-6β-methoxy-3α,5-cyclo-5α-cholestane 24,25-acetonide

A mixture of 0.430 g. (0.0010 mole) of 24S,25-dihydroxy-6β-methoxy-3α,5-cyclo-5α-cholestane, 1.0 ml. (0.010 mole) of 2,2-dimethoxypropane, 9 ml. of acetone and 0.010 g. of p-toluenesulfonic acid monohydrate was stirred at 0° C. for 2 hours. The mixture was diluted with 25 ml. of methylene chloride and this solution was washed wih 10 ml. of saturated aqueous sodium bicarbonate solution and 10 ml. of water. The solution was then dried over anhydrous magnesium sulfate, filtered and evaporated to dryness to yield 0.460 g. (98%) of 24S,25-dihydroxy-6β-methoxy-3α,5-cyclo-5α-cholestane 24,25-acetonide, m.p. 73°–74°; $[\alpha]_D^{25}$ +49.3° (c 1.05, CHCl$_3$).

EXAMPLE 5

24S,25-Dihydroxycholesterol 24,25-acetonide

A mixture of 0.100 g. (0.00025 mole) of 24S,25-epoxy-6β-methoxy-3α,5-cyclo-5α-cholestane, 4 ml. of acetone and 0.005 g. of stannic chloride was stirred at 0° C. for 2 hours. A total of 1 ml. of saturated aqueous sodium acetate solution was added and the mixture was stirred at 0° C. for 5 minutes. The mixture was diluted with 10 ml. of water. This solution was extracted with 3 × 10 ml. of methylene chloride. The combined organic layers were washed with 2 × 10 ml. of saturated aqueous sodium bicarbonate solution. The organic layers were then dried over anhydrous magnesium sulfate, filtered, and evaporated to dryness. The residue was recrystallized from ethyl acetate to give 0.096 g. (84%) of 24S,25-dihydroxycholesterol 24,25-acetonide, m.p. 182°–183°; $[\alpha]_D^{25}$ −33.6° (c 1.11, CHCl$_3$).

EXAMPLE 6

24S,25-Dihydroxycholesterol 24,25-acetonide

A mixture of 0.065 g. (0.000155 mole) of 24S,25-dihydroxycholesterol, 2ml. of 2,2-dimethoxypropane and 0.010 g. of p-toluenesulfonic acid monohydrate was stirrred at 0° for 1 hour. A total of 2 ml. of methanol was added and the mixture was stirred at 25° for 1 hour. The mixture was diluted with 10 ml. of saturated aqueous sodium bicarbonate solution and extracted with 2 × 25 ml. of methylene chloride. The organic layers were washed with 25 ml. of water, dried over anhydrous magnesium sulfate. Evaporation of solvent and recrystallization of the residue from ethyl acetate afforded 0.055 g. (77%) of 24S,25-dihydroxycholesterol 24,25-acetonide, m.p. 182°–183°; $[\alpha]_D^{25}$ −33.0° (c 1.09, CHCl$_3$).

EXAMPLE 7

24R,25-Dihydroxycholesteryl 3-acetate 24,25-acetonide

A mixture of 0.100 g. (0.00021 mole) of 24R,25-dihydroxy-6β-methoxy-3α,5-cyclo-5α-cholestane 24,25-acetonide and 3 ml. of 1.0M sodium acetate in acetic acid was heated at 60° for 18 hours. The mixture was diluted with 10 ml. of water and this solution was extracted with 3 × 10 ml. of methylene chloride. The organic extracts were washed with 2 × 10 ml. of saturated aqueous sodium bicarbonate solution, dried over anhydrous magnesium sulfate, filtered and evaporated to dryness. The residue was recrystallized from pentane to yield 0.090 g. (85%) of 24R,25-dihydroxycholesteryl 3-acetate 24,25-acetonide, m.p. 133°–134°; $[\alpha]_D^{25}$ −42.8° (c 1.02, CHCl$_3$).

EXAMPLE 8

24R,25-Dihydroxycholesteryl 3-acetate 24,25-acetonide

A mixture of 0.080 g. (0.000175 mole) of 24R,25-dihydroxycholesterol 24,25-acetonide, 0.080 g. (0.00078 mole) of acetic anhydride and 1 ml. of pyridine was stirred at 25° for 16 hours. The mixture was diluted with 50 ml. of methylene chloride. This solution was washed with 25 ml. of 10% aqueous sulfuric acid, and 25 ml. of saturated aqueous sodium bicarbonate solution and dried over anhydrous magnesium sulfate. Evaporation of solvent and recrystallization from pentane yielded 0.074 g. (85%) 24R,25-dihydroxycholesteryl 3-acetate 24,25-acetonide, m.p. 133°–134°; $[\alpha]_D^{25}$ −42.5° (c 1.04, CHCl$_3$).

EXAMPLE 9

24S,25-Dihydroxycholesteryl 3-acetate 24,25-acetonide

A mixture of 0.047 g. (0.00010 mole) of 24S,25-dihydroxy-6β-methoxy-3α,5-cholestane, 24,25-acetonide and 1 ml. of 1.0M sodium acetate in acetic acid was heated at 60° for 18 hours. The mixture was diluted with 10 ml. of water and this solution was extracted with 3 × 10 ml. of methylene chloride. The organic extracts were washed with 2 × 10 ml. of saturated sodium bicarbonate solution, dried over anhydrous magnesium sulfate and evaporated to dryness. The residue was recrystallized from methanol to yield 0.042 g. (84%) of 24S,25-dihydroxycholesteryl 3-acetate 24,25-acetonide, m.p. 108°–109°; $[\alpha]_D^{25}$ −37.2° (c 1.04, CHCl$_3$).

EXAMPLE 10

24S,25-Dihydroxycholesteryl 3-acetate 24,25-acetonide

A mixture of 0.040 g. (0.000087 mole) of 24S,25-dihydroxycholesterol 24,25-acetonide, 0.040 g. (0.00039 mole) of acetic anhydride and 0.5 ml. of pyridine were stirred at 25° for 16 hours. The mixture was diluted with 50 ml. of methylene chloride. This solution was washed with 25 ml. of saturated aqueous sodium bicarbonate solution and dried over anhydrous magnesium sulfate. Evaporation of solvent and recrystallization from methanol yielded 0.032 g. (73%) of 24S,25-dihydroxycholesteryl 3-acetate 24,25-acetonide, m.p. 108°–109°; $[\alpha]_D^{25}$ −37.0° (c 1.08, CHCl$_3$).

We claim:

1. A compound of the formula

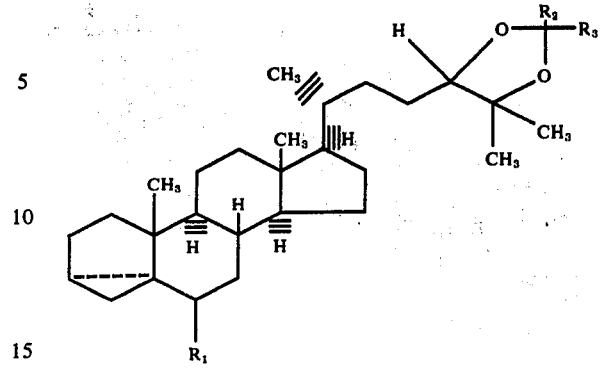

wherein $R_1$ is hydroxy, lower alkoxy, phenyl lower alkoxy, lower alkanoyloxy or benzoyloxy, $R_2$ and $R_3$ each taken independently are lower alkyl, $R_2$ and $R_3$ taken together are lower alkylene and the absolute configuration at C-24 is R or S.

2. The compound of claim 1 wherein $R_1$ is lower alkoxy, $R_2$ and $R_3$ each taken independently are lower alkyl.

3. The compound of claim 2 which is 24R,25-dihydroxy-6β-methoxy-3α,5-cyclo-5α-cholestane 24,25-acetonide.

4. The compound of claim 2 which is 24S,25-dihyroxy-6β-methoxy-3α,5-cyclo-5α-cholestane 24,25-acetonide.

5. A compound of the formula

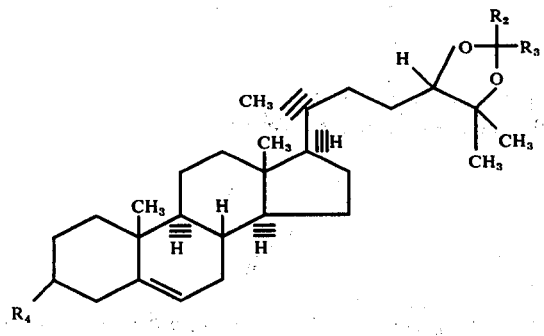

wherein $R_2$ and $R_3$ each taken independently are lower alkyl, $R_2$ and $R_3$ taken together are lower alkylene, $R_4$ is hydroxy or lower alkanoyloxy and the absolute configuration at C-24 is R or S.

6. The compound of claim 5 $R_2$ and $R_3$ each taken independently are lower alkyl, $R_4$ is hydroxy or lower alkanoyloxy.

7. The compound of claim 6 which is 24R,25-dihydroxycholesterol 24,25-acetonide.

8. The compound of claim 6 which is 24S,25-dihydroxycholesterol 24,25-acetonide.

9. The compound of claim 6 which is 24R,25-dihydroxycholesteryl 3-acetate 24,25-acetonide.

10. The compound of claim 6 which is 24S,25-dihydroxycholesteryl 3-acetate 24,25-acetonide.

11. A process for the preparation of a compound of the formula

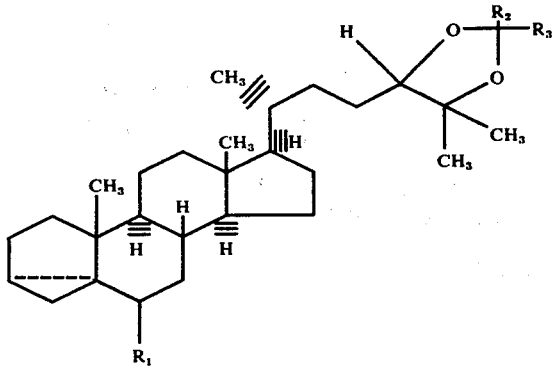

wherein $R_1$ is hydroxy, lower alkoxy, phenyl lower alkoxy, lower alkanoyloxy or benzoyloxy, $R_2$ and $R_3$ each taken independently are lower alkyl, $R_2$ and $R_3$ taken together are lower alkylene and the absolute configuration at C-24 is R or S which comprises contacting a compound of the formula

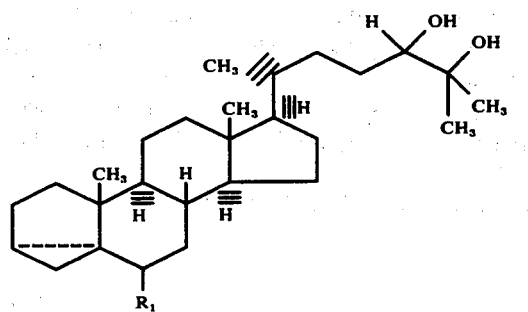

wherein $R_1$ is as above
with a compound of the formula

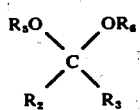

wherein $R_2$ and $R_3$ are as above, $R_5$ and $R_6$ each taken independently are lower alkylene
in the presence of a mineral or organic sulfonic acid in a lower alkanol or lower alkanone.

12. The process of claim 11 wherein $R_1$ is lower alkoxy and $R_2$ and $R_3$ each taken independently are lower alkyl.

13. The process of claim 11 wherein $R_1$ is methoxy and $R_2$ and $R_3$ are methyl.

14. The process of claim 11 wherein the organic sulfonic acid is para-toluenesulfonic acid.

15. The process of claim 11 wherein the alkanone is acetone.

16. The process of claim 11 wherein the reaction temperature is between about −20° and +20° C.

17. The process of claim 11 wherein the temperature is about 0° C.

18. A process for the preparation of a compound of the formula

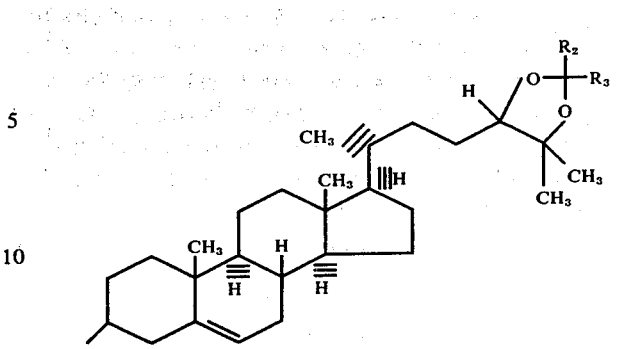

wherein $R_2$ and $R_3$ each taken independently are lower alkyl, $R_2$ and $R_3$ taken together are lower alkylene and the absolute configuration at C-24 is R or S which comprises (a) contacting a compound of the formula

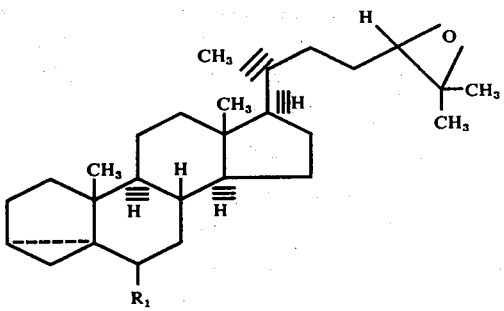

wherein $R_1$ is hydroxy, lower alkoxy, phenyl lower alkoxy, lower alkanoyloxy or benzoyloxy
with a compound of the formula $$R_2-\overset{\overset{O}{\|}}{C}-R_3$$

wherein $R_2$ and $R_3$ are as above
in the presence of a mineral or Lewis acid and (b) adding aqueous base.

19. The process of claim 18 wherein $R_1$ is lower alkoxy and $R_2$ and $R_3$ each taken independently are lower alkyl.

20. The process of claim 19 wherein $R_1$ is methoxy and $R_2$ an $R_3$ are methyl 21. The process of claim 18 wherein the Lewis acid is stannic chloride.

22. The process of claim 18 wherein the base is an alkali metal salt of an organic acid.

23. The process of claim 22 wherein the organic acid is acetic acid.

24. The process of claim 18 wherein, in steps (a) and (b), the temperature is between about −20° and +20° C.

25. The process of claim 24 wherein the temperature is about 0° C.

26. A process for the preparation of a compound of the formula

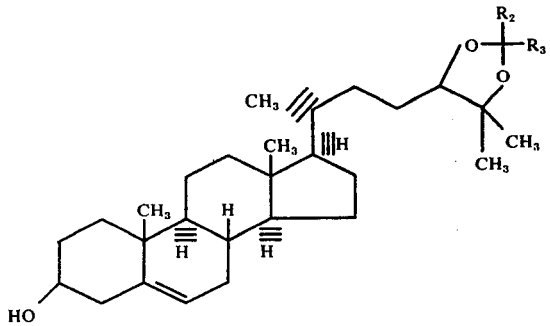

wherein $R_2$ and $R_3$ each taken independently are lower alkyl, $R_2$ and $R_3$ taken together are lower alkylene and the absolute configuration at C-24 is R or S which comprises contacting a compound of the formula

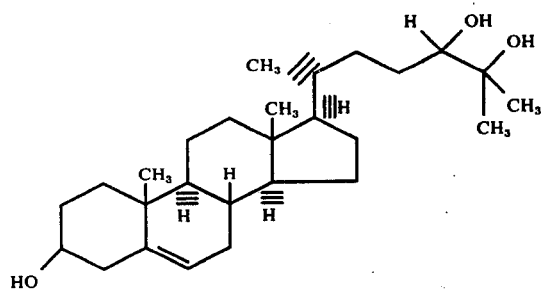

wherein the absolute configuration at C-24 is R or S with a ketalizing agent of the formula

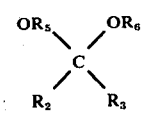

wherein $R_5$ and $R_6$ each taken independently are lower alkyl or $R_5$ and $R_6$ taken together are lower alkylene in the presence of a mineral or organic sulfonic in a lower alkanol or lower alkanone having the same carbon skelton as the ketalizing agent.

27. The process of claim 26 wherein $R_2$ and $R_3$ and $R_5$ and $R_6$ each taken independently are lower alkyl.

28. The process of claim 27 wherein $R_2$, $R_3$, $R_5$ and $R_6$ are methyl.

29. The process of claim 26 wherein the organic sulfonic acid is para-toluenesulfonic acid.

30. The process of claim 26 wherein the temperature is between about $-20°$ and $+20°$ C.

31. The process of claim 30 wherein the temperature is about $0°$ C.

32. The process of claim 26 wherein the ketalizing agent is 2,2-dimethoxypropane.

33. The process of claim 26 wherein the alkanone is acetone.

* * * * *